United States Patent [19]

Onishi et al.

[11] Patent Number: 5,547,576
[45] Date of Patent: Aug. 20, 1996

[54] PATHOGENIC SUBSTANCE REMOVING MATERIAL AND A BLOOD FILTER CONTAINING THE MATERIAL

[75] Inventors: Makoto Onishi; Takashi Ohwada, both of Hadano; Ken Tatebe, Isehara; Yoshitaka Ohmura, Hadano; Kenichi Shimura, Machida, all of Japan

[73] Assignee: Terumo Kabushiki Kaisha, Tokyo, Japan

[21] Appl. No.: 85,813

[22] Filed: Jul. 6, 1993

[30] Foreign Application Priority Data

| Jul. 6, 1992 | [JP] | Japan | 4-178566 |
| Oct. 9, 1992 | [JP] | Japan | 4-270632 |
| Nov. 24, 1992 | [JP] | Japan | 4-313166 |

[51] Int. Cl.$^6$ ............ B01D 63/00; B01D 69/12; B01D 71/60
[52] U.S. Cl. ............ 210/500.37; 210/435; 210/446; 210/490
[58] Field of Search ............ 210/321.6, 321.72–321.78, 210/321.82–321.87, 435, 446, 500.37, 500.38, 500.39, 502.1, 506, 490, 651; 422/101; 502/401, 402; 424/88; 427/488, 535

[56] References Cited

U.S. PATENT DOCUMENTS

| 3,242,073 | 3/1966 | Guebert et al. | |
| 3,352,424 | 11/1967 | Guebert et al. | |
| 4,265,745 | 5/1981 | Kawaguchi et al. | 210/500.37 |
| 4,869,826 | 9/1989 | Wang et al. | 210/679 |
| 5,032,281 | 7/1991 | Nagamatsu et al. | 210/500.37 |
| 5,041,079 | 8/1991 | Takashima et al. | 604/5 |
| 5,049,282 | 9/1991 | Linder et al. | 210/651 |
| 5,133,878 | 7/1992 | Gsell et al. | 210/767 |
| 5,136,032 | 8/1992 | Nagamatsu et al. | 210/500.37 |
| 5,217,627 | 6/1993 | Pall et al. | 210/767 |

FOREIGN PATENT DOCUMENTS

| 267286 | 5/1988 | European Pat. Off. |
| 474267 | 3/1992 | European Pat. Off. |
| 2-167232 | 6/1990 | Japan |
| 3-123630 | 5/1991 | Japan |
| 2238055 | 5/1991 | United Kingdom |
| 82/01477 | 5/1982 | WIPO |

OTHER PUBLICATIONS

Database WPI, Derwent Publications Ltd., London, GB; of Japanese Patent No. 05 084 071, Issued Apr. 6, 1993.
Database WPI, Derwent Publications Ltd., London, GB; of Japanese Patent No. 62 039 636, Isssued Feb. 20, 1987.
Database WPI, Derwent Publications Ltd., London, GB; of Japanese Patent No. 03 123 630, Issued May 27, 1991.

*Primary Examiner*—John Kim
*Attorney, Agent, or Firm*—Burns, Doane, Swecker & Mathis, L.L.P.

[57] ABSTRACT

A material wherein a polyamine compound is immobilized on its base surface and a blood filter using this material. The material is provided in the form of a porous membrane having the maximum pore diameter of 0.1–50 μm. The polyamine compound is at least one compound selected from the group consisting of (a) a polyamine compound which has primary and secondary amines in its molecule and a hydrophobic part between these amines, (b) a polyamine compound represented by the following formula (I);

$$\left(\begin{array}{c} R^1 \\ | \\ C \\ | \\ R^2 \end{array} - \begin{array}{c} R^3 \\ | \\ C \\ | \\ R^4 \end{array} - N \right)_{\overline{n}} \quad (I)$$

wherein $R^1$, $R^2$, $R^3$, $R^4$ and $R^5$ represent hydrogen, aliphatic and aromatic hydrocarbons, and halogen, and n is 5 or more, and (c) a polyamine compound represented by the following formula (II);

$$\left(CH_2 - \begin{array}{c} CH \\ | \\ R \end{array}\right)_{\overline{n}} \quad (II)$$

wherein R represents $NH_2$ or aminoalkyl radical having 1 to 4 carbon atoms and n is 5 or more. The blood filter comprises a housing which has an inlet and outlet, and the material arranged inside the housing.

7 Claims, 1 Drawing Sheet

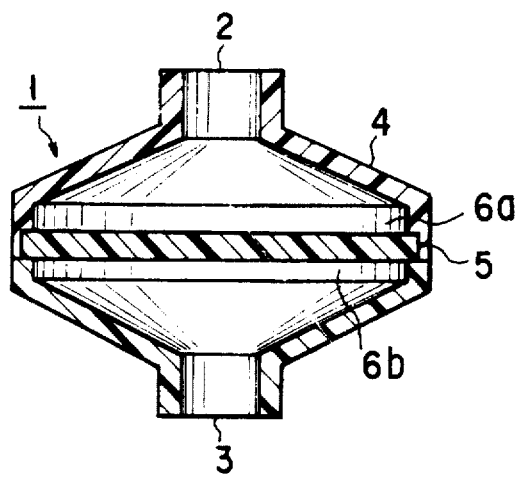
F I G. 1
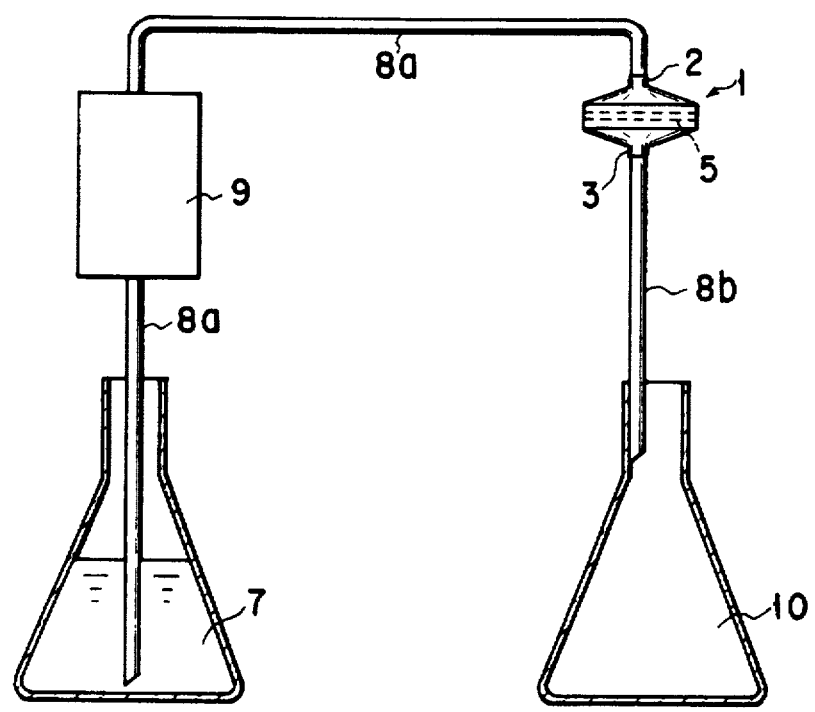
F I G. 2

PATHOGENIC SUBSTANCE REMOVING MATERIAL AND A BLOOD FILTER CONTAINING THE MATERIAL

BACKGROUND OF THE INVENTION

1. Field of the Invention

The present invention related to a material which can selectively remove pathogenic substances containing leukocytes, platelets and virus from a protein containing solution.

2. Description of the Related Art

Currently in the field of medical care, the need to more drastically and selectively remove virus, leukocytes, platelets, etc. from the body fluid such as blood and plasma is increasing all the more. For example, it is an accepted criterion that the blood for transfusion should not contain virus, and that, as a rule, component transfusion should give only the blood component required for the patient and no unnecessary components. However, despite the fact that it is called component transfusion, the concentrated erythrocyte preparations in general use actually contain a large quantity of leukocytes and platelets. When such concentrated erythrocyte preparations are transfused to the patients who should frequently receive transfusion (those with aplastic anemia, hemolytic anemia, chronic hemorrhagic anemia, etc.), antibody against to leukocytes and platelets is produced, and there is also a possibility of transfusion reactions. To inhibit the generation of antibody to leukocytes and platelets and to prevent transfusion reactions, it is necessary to provide erythrocyte preparations of high purity by removing leukocytes and platelets therefrom. Recently Graft-versus-Host Disease (GVHD) is posing a problem. In this disease, the lymphocytes with division potential which are present in the transfused blood acknowledge the histocompatibility antibody of the patient as the foreign matter and attack it. For this reason as well, the demand for the blood preparations from which leukocytes are removed is on the increase. To this end, it is necessary to remove lymphocytes from the blood for transfusion by a blood filter or to destroy the division potential of lymphocytes by radiation.

In the method using radiation, 1500 rad (15 Gy) of radiation is irradiated at blood preparations containing lymphocytes (fresh blood, preserved blood, concentrated erythrocyte preparations, concentrated platelet preparations, etc.) to destroy the division potential of lymphocytes. In Japan, the irradiation to blood bags is conducted mainly by X ray operators in the radiotherapeutic room. It takes about 5 or 6 minutes to irradiate one batch. In USA and Europe, an exclusive device for irradiation at blood preparations using $Cs^{137}$ as the source is commercialized. With this device, it is possible to irradiate a 400 to 500 ml blood bag in 2 to 6 minutes. According to the report by Leitman et al., a function of erythrocytes, the platelet or granulocyte is not affected at this dose (Transfusion 25 (4): 293–300, 1985). However, as this method requires expensive equipment as well as the control system administered by a person responsible for the operation, it is not a universal way for everyone to practice everywhere.

On the other hand, there is a method in which a fiber filter for filtration is used to separate leukocytes by adhering them to the filter. The method takes advantage of a property of leukocyte that it tends to adhere to somewhat hydrophobic curved surface with low curvature. Filter material is prepared by laminating porous matters or fibers with small diameter, and blood corpuscles are captured when the fluid containing blood corpuscles is passed through the filter. An advantage of this method is that it is easy to handle and inexpensive. However, since leukocytes are physically captured in this method, there is a problem that complete removal of leukocytes as in the case of irradiation cannot be expected. In other words, the removal rate is increased in fresh blood in which intense acknowledgment of leukocytes is possible while sufficient removal of leukocytes is doubtful in preserved blood which offers less recognition of leukocytes. To be more precise, the filter should has an ability of recognizing and capturing leukocytes to capture leukocytes in preserved blood.

As the adsorption separation system taking advantage of selective recognition mechanism, the column method using adhesive beads is well known. For example, there are dextran sulfate-fixed beads used in the medical field which selectively adhere and remove low density lipoprotein (LDL) from the plasma, and the affinity chromatography used as a purification technique in the biochemical field.

As a method which impart the function to selectively recognize cell, virus or biologically derived substance to the membrane surface, there is a method to take advantage of the selective recognition function of a living body, for example, antigen—antibody, enzyme—substrate and receptor on the cell surface. However, this is an expensive method since the substance used as a ligand should be biologically derived protein and is therefore vulnerable to heat and acid, making it difficult to sterilize and handle.

Zierdt and others reported that they found particles such as bacteria, erythrocytes, leukocytes, platelets and polystyrene beads could still be captured when a fluid containing the particles were filtered through a membrane having a larger pore size than the particle size (Applied and Environmental Microbiology, 1979, 12, 1166–1172). They concluded that the capture was attributable to a electrostatic interaction since particles were not captured by the membrane treated with anion surfactant, and indicated that it would be possible to adhere and capture leukocytes and platelets through electrostatic interaction by means of surface electric charge.

In this regard, there is a description in U.S. Pat. Nos. 3,242,073 and 3,352,424 on the removal of platelets having negative surface charge from a fluid by using a filter material which is prepared by electrostatically binding cationic organic poly-electrolytes to anionic filter. In Unexamined Published Japanese Patent Application No. 3-207413, a filter material which possesses quarternary ammonium groups on the surface and positive zeta potential at pH 7 is described. However, when the blood is filtered through such cationic filter, the concentration of the factors released from platelets goes up and thus deteriorates the quality of blood preparations after filtration despite the improved capture rate of leukocytes and platelets.

On the other hand, isoelectric point (pI) of many virus particles is 3–6, and thus they have negative charge in the neutral range, adhesion of virus is possible through electrostatic interaction from the water containing less impurities. As the material for removing virus, there are porous membrane and material having polycationic structure on the surface such as polyvinyl pyridinium described in Unexamined Published Japanese Patent Application No. 3-123630. However, it was difficult to selectively remove virus with conventional cationic filter since non-specific adsorption of protein to the cationic surface occurs in a solution with high protein concentration such as plasma and blood.

As a filter to remove virus from body fluid and protein containing solution, regenerated cellulose membrane described in Unexamined Published Japanese Patent Application No. 2-167232. As the pore size of this membrane is smaller than that of virus particle, virus cannot pass through the membrane. However, the transmission speed is low due to the small pore size, and clogging of the membrane often occurs.

As a material to separate virus from blood and plasma by making use of biological affinity, International Patent Publication No. WO 89/01813 describes a material in which the receptor of the virus existing on the cellular surface is fixed to its surface. However, the process of purifying receptor from cell and that of binding the receptor to the base are complicated in this method. Furthermore, the use of biologically derived component creates problems of cost, functional stability and time course change.

Though the membrane technology used for separation is a technology widely used in the industry through researches on ultrafiltration membrane, reverse osmosis membrane, ion exchange membrane, gas separation membrane and osmotic gasified membrane. However, most of them are based on the separation through the difference in concentration, pressure and potential making use of membrane pore, and there are few separation membranes designed by positively introducing selective recognition mechanism into the membrane surface.

SUMMARY OF THE INVENTION

The present invention aims at providing a material which can selectively remove pathogenic substances containing leukocytes, platelets and virus from a protein containing solution, and which may constitutes a membrane with excellent processing speed and easy to handle when used as a porous membrane and the like.

The present invention also aims at providing a blood filter which is equivalent to or better than conventional blood filter in terms of capture rate of blood corpuscle such as leukocytes and platelets, and which has overcome the shortcoming of conventional blood filter that an increase in the concentration of factors released from platelets deteriorates the quality of blood preparations after filtration.

The material of the present invention that selectively removes pathogenic substances, hereinafter the material being referred to as pathogenic substance selectively removing material, is the one characterized in that it can selectively remove pathogenic substances from a protein containing solution and contains a base to which surface a polyamine compound is immobilized.

In the pathogenic substance selectively removing material of the present invention, the compounds described in (a) through (c) are preferably used as polyamine compound.

(a) Polyamine compound having primary and secondary amines in its molecule and hydrophobic part between these amines, (b) Polyamine compound represented by the following formula (I);

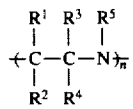

wherein, $R^1$, $R^2$, $R^3$, $R^4$ and $R^5$ represent a substituent, respectively, such as hydrogen, aliphatic and aromatic hydrocarbon and halogen and n is 5 or more, (c) Polyamine compound represented by the following formula (II);

wherein R represents $NH_2$ or the aminoalkyl radicals having 1 to 4 carbon atoms, and n is 5 or more.

The pathogenic substance selectively removing material of the present invention is preferably provided in the form of porous membrane and its maximum pore size is preferably 0.1–50 μm.

It is easy to handle the pathogeic substance selectively removing material of the present invention since polyamine compound is immobilized in the surface of the material, and when this material is provided in the form of a porous membrane, an excellent membrane which allows simple and speedy processing will be obtained.

The pathegeic substance selectively removing material of the present invention is preferably used for removing virus, leukocytes and platelets contained in a protein containing solution such as body fluid including blood and plasma. In addition, it is also useful in the research for cell recognition, separation, and concentration and the construction of culture systems. Furthermore, since it is able to recognize and remove virus in an environment in which protein or the like exist, i.e. plasma, it can be effectively used in the prevention of virus contamination and virus infection in the food industry, fermentation industry, pharmaceutical industry and medical institutions.

The blood filter of the present invention comprises a housing which has fluid inlet and outlet and the said material of the present invention that selectively removes pathogenic substances arranged inside the said housing.

The pathogenic substance selectively removing material used for the blood filter of the present invention is preferably in the form of porous membrane, and more preferably having the maximum pore size of 5–50 μm.

The blood filter of the present invention can improve the removal rate of leukocytes and platelets from blood without activating platelets. Therefore, it is possible to provide safe and high quality blood preparations by using the blood filter of the present invention.

BRIEF DESCRIPTION OF THE DRAWINGS

FIG. 1 is a sectional view indicating one embodiment of the blood filter of the present invention; and FIG. 2 is a schematic view showing an example of the blood processing device in which the blood filter of the present invention is incorporated.

DETAILED DESCRIPTION OF THE PREFERRED EMBODIMENTS

Polyamine compound is a compound which every living body possesses whether it is a eucaryotic cell or procaryotic cell. The compound is known to act on various biological polymers including cell membrane and nucleic acid which have abundant negative charge to influence their functions (refer to "Kagaku to Seibutsu" or Chemistry and Biology, vol. 28, No. 3, 162–171, 1991 by Akira Shirahata; The Physiology of Polyamines, ed. by U. Bachtach and Y. M. Helmet, CRC Press, Boca Raron, 1989; The Biochemical Journal, vol. 260, pages 1–10, 1989, F. Schuber).

On the other hand, the polyvalent cationic compound such as polyvinyl pyridinium that has quaternary ammonium structure in the molecule and the compound having hydrophobic radicals demonstrate strong interaction with protein. As a result, non-specific adsorption increases and the cell and virus selectivity is lost in these compounds in the existence of protein as seen in blood and liquid culture medium. Many cells have glycoprotein having negative charge on the cell surface and are known to electrostatically bind to high molecular weight polycations. However, as an interaction is too intense in the high molecular weight polycations such as strongly basic compound having quaternary ammonium salt and the compound having hydrophobic part, the damage to cells and to cell selectivity becomes large. While the polyamine compounds used for the material of the present invention possesses basicity and molecular structure which act easily on cells and virus, its low degree of interaction with the coexisting protein makes it possible that the material selectively capture cells and virus.

Even a simple virus found in a vertebrate has several proteins and polypeptides but very complicated virus, e.g. pox virus, has over 100 kinds of these substances. A simple virus which does not have an envelope is encased in a protein shell called capsid. In the virus which has an envelope, a glycoprotein called peplomer which projects from the envelope exists on the surface of virus particle. For this reason, the virus particle has either positive or negative surface charge. Many viruses have anionic part derived from anionic phospholipid, sialic acid, or capsid protein, and are known to adsorb through electrostatic interaction to high molecular weight polyvalent cations. However, selective adsorption of virus is not possible in an environment such as liquid culture medium and plasma, in which protein coexist, since the electrostatic interaction is too intense in a strongly basic compound having quaternary ammonium salt and high molecular weight polycation which possesses hydrophobic part.

Among polyamine compounds, polyethyleneimine is an optimal material for ligand since it is a water soluble polymer which has many amines in its molecule, and is low price. Since interaction with protein is comparatively weak in polyethyleneimine itself, non-specific adsorption of protein is suppressed and selective adsorption of virus is possible by controlling the amount of its surface presence even when it is immobilized to the surface of the base.

The pathogenic substance selectively removing material of the present invention is a material which can remove pathogenic substances such as virus, leukocytes and platelets from a protein containing solution. Some of the examples of protein containing solutions are body fluid such as blood, plasma, serum and urine, liquid culture medium of cell and microorganism or a solution containing protein component derived from these fluids. The pathogenic substance selectively removing material of the present invention is a material which can selectively adhere and remove pathogenic substances from a fluid particularly containing plasma and plasma protein.

The pathogenic substance selectively removing material of the present invention has polyamine compound immobilized to its base surface. As a polyamine compounds used in the present invention, the following compounds are preferable.

(a) Polyamine compound which has primary or secondary amines in the molecule and has hydrophobic part between these amines, (b) Polyamine compound represented by the following formula (I);

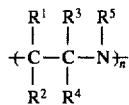

wherein $R^1$, $R^2$, $R^3$, $R^4$ and $R^5$ indicate a substituent, respectively, such as hydrogen, aliphatic or aromatic hydrocarbon and halogen, and n is 5 or more, and (c) Polyamine compound represented by the following formula (II);

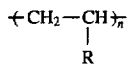

wherein R indicates $NH_2$ or aminoalkyl radicals having 1 to 4 carbon atoms, and n is 5 or more.

Each of these compounds may be used alone or in combination thereof.

An example of polyamine compound which has primary or secondary amines in the molecule and has hydrophobic part between these amines is aliphatic polyamine. To be more precise, spermidine and spermine known as biological polyamines may be preferably used. These polyamines are characterized in that as the basic structure, they have amino groups (primary amine) at the terminal part of the molecule and imino groups (secondary amine) in the molecule. Between the amino groups and imino groups, hydrophobic part formed by hydrocarbon or halogenated hydrocarbon. Tertiary amino groups are not always necessary.

In the polyamine compound used in the present invention, the sum of said amino groups and imino groups is preferably 3 or more. If the sum is smaller than 3, the interaction with the substances to be adsorbed tends to become less due to the small amount of amine. Though the structure of the hydrophobic part is not particularly restricted, it is preferable that the hydrophobic part is an aliphatic hydrocarbon having a double bond in its molecule. More preferably, the hydrophobic part is an alkylene group such as methylene chain $—(CH_2)_n—$. Preferably n is 2–20, or more preferably between 3 and 10. When it is 2 or more, the hydrophobic part may demonstrate its function. Furthermore, if n is 20 or more, the effect is not produced, since the solubility of the compound in water type solvent is lowered or non-specific protein adsorption is increased by hydrophobic interaction due to too high molecular weight.

As a preferable example of polyamine compound represented by the above formula (I), polymer or copolymer of aziridine compound may be given. Aziridine compound herein means a compound which contains at least 1 aziridine group in one molecule, and more concretely a compound represented by the following formula (III);

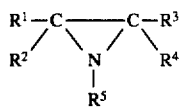

wherein $R^1$, $R^2$, $R^3$, $R^4$ and $R^5$ in the formula have the same meanings as defined in the above formula (I).

As concrete examples of polymer or copolymer of aziridine compound, a polymer having ethyleneimine, propyleneimine, butyleneimine or N-hydroxyethyl ethyleneimine, N-aminoethyl ethyleneimine as a monomer unit, a polymer such as polyethyleneimine or polypropyleneimine, mutual copolymer of the above monomers or a copolymer with other copolymeric monomer may be given. A block copolymer or graft copolymer with a polymer of having at its end the functional group which can react with a polymer or copolymer of aziridine compounds shown above may also be preferably used in the present invention. In this case, the ratio of aziridine compound shall be at least 5 mol % or more, and preferably 20 mol % or more. The examples further include cyclic polyamines of aziridine compound such as cyclamic or bicyclamic compound and their derivatives. As the polyamine compound used in the present invention, polyethyleneimine, i.e. polymer or copolymer of ethyleneimine, or cyclic polyamine compound is preferable.

As examples of the compound represented by the above formula (II), polyvinylamine and polyallylamine may be given.

The material of the base to which said polyamine compound is immobilized is not particularly restricted. For example, it may be natural polymer such as cellulose and its derivatives and polymer materials such as polyolefin, polyamide, polyimide, polyurethane, polyester, polysulfon and polyacrylnitril.

It is preferable not to immobilize a large amount of the above polyamine compound which might completely cover the base surface. For example, it is preferable to provide the ratio of polyamine compound on the base surface at 60% or less, or more preferably at 40% or less in terms of carbon atoms when surface analysis using ESCA is performed on the dry base. More concretely, for example, when polyethyleneimine is immobilized on a polyolefin material, the ratio of nitrogen atoms to carbon atoms (N/C) is preferably 0.005–0.2, or more preferably 0.01–0.1. If the ratio exceeds 0.25, polyethyleneimine will cover 60% or more of the base surface, which intensifies the interaction with protein and thus lowers the function to selectively remove pathogenic substances. When the base itself contains nitrogen atoms, the presence ratio of the polyamine compound may be calculated by correcting the ratio with the N/C ratio of the base.

Immobilization of a polyamine compound to the base surface means that it is bound to reactive functional groups on the surface of the base so that the polyamine compound does elute from the surface. The binding of polyamine compound and reactive functional groups shall preferably be done by covalent bond. The amount of polyamine compound immobilized to the base material may be measured by titration using perchloric acid. When the phathogenic substance selectively removing material is provided in the form of porous membrane, the amount of polyamine compound immobilized to the surface of base material is preferably $1 \times 10^{-4}$ eq/g or more, or more preferably $4 \times 10^{-4}$ eq/g or more.

As a method to immobilize polyamine compound to the surface of base material, it is possible to use any methods known in this field. For example, after introducing functional groups such as epoxy groups, amino groups, aldehyde groups, carboxyl groups, hydroxyl groups and acid chloride groups by graft polymerization method, coating method, chemical modification and oxidization, polyamine compound may be immobilized by reacting amino groups thereof with the functional groups directly or via coupling agent or spacer to the surface of base material.

Though it is possible to immobilize polyamine compound by the above method, it is preferable in the present invention to immobilize polyamine compound by a method comprising a process to introduce surface graft radicals having reactive functional groups to the surface of base material and a process to immobilize the polyamine compound to these reactive functional groups. Surface graft radicals having reactive functional groups are a graft chain which has as the component a monomer having acid halogen radicals, isocyanate radicals and epoxy radicals, etc. in its molecule.

Examples include (metha)acrylic halide such as (metha)acrylic chloride and (metha)acrylic bromide, (metha)acryloyloxyalkyl isocyanate such as 2-(metha)acryloyloxyethyl isocyanate, 3-(metha)acryloyloxypropyl isocyanate, 4-(metha)acryloyloxybutyl isocyanate, (metha)acryloyloxyisopropyl isocyanate, 2-(metha)acryloyloxy- 1-ethylmethylethyl isocyanate, 2-(metha)acryloyloxy- 1-ethylethylisocyanate, 4-(metha)acryloyloxy- 2-ethylbutyl isocyanate, 2-(metha)acryloyloxy- 2,2-dimethylethyl isocyanate, and a monomer containing epoxy groups such as 2,3-epoxypropyl (metha)acrylate, 3,4-epoxybutyl (metha)acrylate, 2,3-epoxyisobutyl (metha)acrylate, 3,4-epoxy-1 -methylbutyl (metha)acrylate, 2,3-epoxy-1-methylethyl acrylate. In the present invention, graft chain composed by monomer having epoxy groups such as glycidyl acrylate or glycidyl methacrylate is preferable.

As the graft chain introduced into the base surface, either one type alone may be used or more than 2 types may be used in combination. After introducing precursors thereof into the base surface, functional groups may be converted by chemical treatment into acid halogen groups, isocyanate groups and epoxy groups, etc. for reaction with polyamine compound.

As a method to form a graft chain on the base surface, any of the known methods may be used. However, the preferable method is to generate radicals on the base surface by plasma irradiation, and then form a surface graft chain by making use of the radicals. When a monomer reactive to the radicals is provided, it may be in fluid form. However, considering the operability and safety, it is preferable to provide a gaseous monomer for polymerization. The pressure at the time of providing the gaseous monomer is preferably 0.001–100 Torr, more preferably 0.01–50 Torr, and most preferably 0.1–10 Torr. In view of the operability, the time consumed is preferably 10 seconds–2 hours, more preferably 30 seconds–1 hour, and most preferably 1 min–30 minutes. This method is assumed to be preferable for the following reasons. Microscopically, the surface graft chain having reactive functional groups, e.g. polyglycidyl acrylate, exists in phase separation from the surface of the base material, e.g. polypropylene. For this reason, the polyamine compound bound to the reactive functional groups is also microscopically assumed to exist in phase separation on the surface of base material. As a result, the amount of polyamine compound on the surface becomes smaller. Furthermore, as the polyamine compound is localized or phase-separated in such a way as to decrease the interaction between the protein in the sample and base material surface, non-specific adsorption of protein to the base material surface is decreased. As a result, the pathogenic substance removal function is easily displayed. On the other hand, the above effect is not observed in the method in which reactive functional groups are introduced to the base surface by coating method or the method in which the polyamine compound is bound to the functional groups possessed by the base itself. As a result, non-specific adsorption of protein tends to increase.

The form of the pathogenic substance selectively removing material of the present invention is not particularly restricted. For example, it may be in an arbitrary form of beads, hollow fiber, flat membrane, unwoven cloth, woven cloth or porous membrane comprising tube-like porous body, but preferably in the porous membrane form. Porous membrane herein means a membrane having through holes which allow filtration of test sample. In the present invention, the membrane is preferably consisted of a base material prepared by forming a hydrophobic material such as polypropylene or polyvinylidene fluoride which has excellent dimensional stability and demonstrates low swelling against water into a membrane, and then by giving hydrophilic property to the membrane surface by surface treatment with coating of such hydrophilic polymer or graft polymerization.

When the form of the pathogenic substance selectively removing material of the present invention is porous membrane, the values related to the porous membrane such as pore size depend on the object to capture, membrane thickness, lamination of the membrane, i.e. number of layers laminated or the like. It is desirable to set these values within a range which does not allow clogging when the membrane is made into module and yet does not lower the removal rate. In the present invention, the material is preferably in the form of porous membrane with the maximum pore size of 0.1–50.0 μm, void volume of 20–95%, water transmission rate of 10 ml/min/m$^2$/mmHg or more, or unwoven cloth in which a large number of filaments with the average diameter of 100 μm or less are crossed.

In the case of porous membrane, if the maximum pore size is less than 0.1 μm, fluid transmission speed becomes slow and the possibility of clogging is high. On the other hand, if the pore size exceeds 50.0 μm, the interaction with the object to be adsorbed becomes insufficient. If the void volume is less than 20%, sufficient transmission speed is not achieved, but if it exceeds 95%, a problem in the physical strength may arise. If the water transmission rate is less than 10 ml/min/m$^2$/mmHg, the transmission pressure tends to increase. To be more precise, it is preferable that the maximum pore diameter of the porous membrane is 0.1–5 μm for plasma and culture solution, and 5–50 μm if cells are contained in the sample. When the phathogenic substance selectively removing material of the present invention is provided in the form of porous membrane, the most preferable maximum pore diameter is 0.2–1.0 μm, void volume 40–90% and water transmission rate 100 ml/min/m$^2$/mmHg or more. The values shown herein are those obtained when said polyamine compound is immobilized on the base surface. It is preferable to immobilize polyamine compound not only on the outer surface of the membrane but also into the inner surface of pores.

When the material of the present invention is used in the form of unwoven cloth, filaments which form this cloth may be either monofilaments or multifilaments. The average diameter of filaments is preferably 100 μm or less, but more preferably 50 μm or less at which size it is possible to increase the surface area of the cloth, thereby increasing the adsorbing part.

For the material of the present invention to selectively remove pathogenic substances from a protein containing solution, it is preferable that the adsorbing property of the material surface is low. When the material is provided in the form of porous membrane, it is preferable that the surface is improved with flexible polymers having non-swelling property against water, i.e. having swelling rate of 20% or less, and the glass transition point of 290K or less to maintain sufficient transmission function without clogging the pores. Examples of such polymer include polymers and copolymers having monomers of alkoxyalkyl acrylate such as methoxyethyl acrylate as a major component.

For the removal of pathogenic substances by the material of the present invention, it is sufficient to have the material of the present invention bring into contact with the fluid containing pathogenic substances. To be more precise, this is carried out by batch system including immersion method, flow system making use of various forms of column and filtration system using a filter, but it is most preferable to apply filtration system using a filter. In addition to applying the material of the present invention by the above mentioned systems in known separation method and separation device using columns and membrane modules, it may also be used by itself as well as in combination by kneading, inner packing and lamination with other material to be made into health control products and pharmaceutical products for the purpose of prevention and diagnosis of virus infection or the like.

Though the pathogenic substance selectively removing material of the present invention may be used for various purposes, it is preferably employed for detection, separation, preservation and culture of viruses, bacteria and cells since it has affinity to and biological activity in many viruses, bacteria and cells. In particular, it is useful in selectively recognizing cells and viruses in an environment in which protein coexists.

In the present specifications, the word "virus" refers not only to a virus in complete form but also to its fragment. "Selective removal of virus" means not only physically removing virus but also inactivate or decrease the virus activity and lower or eliminate the virus infection. The capacity of virus removal is evaluated by measuring how much of the marker virus ($10^2$ pfu/ml or more) added to the fluid before filtration is captured or removed not by the separation owing to size but by the interaction with the material surface. As a marker virus, herpes virus (HSV-1), φX174 and AIDS virus (HIV) may be used. It is preferable that based on the above definition the pathogenic substance selectively removing material of the present invention demonstrates the virus removal rate of at least 90%, preferably 99% or more, against a plural types of viruses with different properties.

The pathogenic substance selectively removing material of the present invention may be used to remove virus from a fluid such as plasma, in which protein exits in mixture. It is also preferably used in an environment with risk of virus infection through dispersion of and contact with blood and body fluid. Examples of such application include medical tools used in the medical institutions and first aid treatment in relation to, or daily commodities used by those infected with virus or likely to become infected, daily commodities used by healthy people for the purpose of preventing virus infection and back up use concurrently used with virus inactivation method making use of heat and drugs. Furthermore, it may also be used in a product such as air filter which provides virus-free environment.

The present invention also provides a blood filter which uses the pathogenic substance selectively removing material. The blood filter of the present invention is a filter intended for the removal of platelets and/or leukocytes from a fluid containing platelets and leukocytes, and is mainly intended for the production of and treatment with blood preparations.

In the blood filter of the present invention, above described pathogenic substance selectively removing material is used as a filter material. Though the form of said material used as a filter material is not particularly restricted, unwoven cloth or porous body with the maximum pore size of 5–50 μm is preferable. When this filter material is incorporated into a blood filter, it may take an arbitrary form such as lamination, roll, hollow fiber and random type. As the polyamine compound immobilized on the filter surface, a compound represented by the formula (I) or (II) in the above is preferable, but polymer or copolymer of aziridine compound is more preferable.

The shape of a blood filter is not particularly restricted. It may take an arbitrary shape such as cylindrical and disk-like or rhombic cross-section and square cross-section, but it must have a blood inlet and an outlet for passing blood component in contact with the filter material. The form of the filter material to be incorporated into a blood filter is not particularly restricted. It may be provided in lamination of several layers or in combination with different type of filter material.

The blood filter of the present invention is described in more detail by referring to the drawing. FIG. 1 shows the cross section of one embodiment of the blood filter of the present invention. The blood filter shown in FIG. 1 comprises a housing 4 which has a blood inlet 2 and a blood outlet 3 and a filter material 5 provided between supporting members 6a and 6b inside the housing 4. The filter material 5 is positioned so as to intercept the passage from the blood inlet 2 to the blood outlet 3 in the housing 4, and the peripheral portion of the filter material 5 or/and the supporting members 6a and 6b are closely joined with the inner wall of the housing 4 so as to make all the blood flowing into the housing 4 pass through the filter material 5. Porous membrane is used as the filter material 5, and the blood which flows from the blood inlet 2 to the housing 4 passes through the filter material 5 and then the blood outlet 3 to be discharged outside.

FIG. 2 is a schematic plan of one example of blood processing device using this blood filter 1. In this device, a fluid introducing tube 8a is connected to the blood inlet 2 of the blood filter 1, and this fluid introducing tube 8a is led into concentrated erythrocyte fluid 7 in a container via a suction pump 9. A fluid introducing tube 8b is connected to the blood outlet 3 of the blood filter 1, and this fluid introducing tube 8b is led inside the blood recovery container 10. When the suction pump 9 is worked, the concentrated erythrocyte fluid 7 flows from the blood inlet 2 through the blood introducing tube 8a into the blood filter 1. The concentrated erythrocyte fluid which flowed into the blood filter 1 passes through the filter material 5 with contacting it. During this process, the concentrated erythrocyte fluid is processed and thus platelets, leukocytes, etc. in the fluid are removed. The concentrated erythrocyte fluid which passed through the filter material 5 flows from the blood outlet 3 to outside the blood filter 1. The processed concentrated erythrocyte fluid which flowed from the blood outlet 3 is collected into the blood recovery container 10 through the fluid introducing tube 8b.

The blood filter of the present invention less activates platelets even though it improve platelet removal rate. In other words, the blood filter of the present invention is capable of favorably and securely removing not only leukocytes but also platelets, and since it activates platelets less, factors such as β-TG and serotonin released by activation of platelets do not enter the filtrate to deteriorate the quality of the processed blood.

The polymer or copolymer of aziridine compound which is preferably used as a polyamine compound immobilized on the filter material surface of the blood filter of the present invention mainly has secondary or tertiary amino groups which are weak basic anion exchange groups in its molecule. For this reason, the electrostatic interaction with platelets becomes weak compared to that of polycationic compound having quaternary ammonium groups which are strong basic anion exchange groups in its molecule. By controlling the molecular weight, it is possible to easily control the interaction with platelets in the case of a polymer of aziridine compound. Due to this property, it is possible to obtain a surface which can capture platelets without activating them. In the blood filter of the present invention, polyethyleneimine among aziridine compounds is particularly preferable since it is inexpensive and easily obtainable. Its average molecular weight is preferably 500–8,000 and more preferably 600–3,000 for the purpose of providing a balance between the activation and adsorption of platelets on the filter material surface. The molecular weight and charge density of the polymer of aziridine compound immobilized on the filter material surface have considerable influence on the adsorption and activation of platelets. For example, when polyethyleneimine having a large molecular weight is immobilized on the surface, the charge as polycation becomes large, resulting in a tendency to activate platelets and damage cellular membrane. On the other hand, when polyethyleneimine having a small molecular weight is immobilized, the electric charge density becomes smaller and thus it is difficult to improve the platelet removal rate.

The present invention is described in more detail by the following examples. The property values of the pathogenic substance selectively removing material which are described in the present specifications including the following examples were measured under the conditions and/or by methods given below.

a. Water transmission rate was determined under the pressure of 0.7 kg/cm² and at 25° C.±2° C.

b. Void volume was calculated by the following formula (A).

$$\text{Void volume (\%)} = \{(\text{Volume of void part})/(\text{Volume of void part} + \text{volume of substantial part of porous body})\} \times 100 \quad \text{(A)}$$

c. With reference to ASTM-F316, the maximum pore size of the membrane was obtained from the value measured by the bubble point method using isopropyl alcohol as a solvent. The maximum pore size is the value which indicates the maximum pore diameter of the pores which uniformly exist over the membrane after its formation, and does not include larger pores of pin holes and large holes having a larger diameter than the maximum pore diameter which are generated after membrane formation.

d. Filament diameter is the mean value of lengths of the major and minor axes of filaments observed by a scanning electron microscope. The value obtained is regardless of the filament form. The filament may be modified filament or porous filament.

e. Plaque method was used for the assay of virus. To be more precise, the specimen was contacted with host cell or host bacterium, and the number of plaques generated by virus infection was obtained. The virus removal rate (virus capture rate) was calculated from the following formula (B) on the basis of this value.

$$\text{Virus removal rate (\%)} = \{(1 - \text{number of surviving viruses})/(\text{number of viruses in the stock solution})\} \times 100 \quad \text{(B)}$$

EXAMPLE 1

A. Manufacture of polypropylene porous membrane

Per 100 parts by weight of the mixture of 2 types of polypropylenes (mixture weight ratio 100:40) having melt flow index of 30 and 0.3 respectively, 320 parts by weight of liquid paraffin (number-average molecular weight 324) and 0.3 part by weight of 1,3,2,4-bis(p-ethylbenzylidene) sorbitol as a crystal nucleus forming agent were melted and kneaded into pellets by a biaxial extruder. Using said extruder, these pellets were melted at 150°–200° C. and extruded through a T die with the slit width of 0.6 mm. Cooling and setting solution comprising polyethylene glycol was arranged immediately under the T die. The melted product excruded into the air was led into the cooling and setting solution by rotating a guide roller provide in the solution, thereby cooling and setting the product, after which it was rolled off. The rolled film was cut into a prescribed length and immobilized in both the longitudinal and lateral directions, immersed in 1,1,2-trichloro-1,2,2-trifluoroethane for 10 minutes×4 times (total of 40 minutes), and the liquid paraffin was extracted. This was subsequently heat treated for 2 minutes in the air at 135° C. to obtain a polypropylene porous membrane with the maximum pore diameter of 0.5 μm, void ratio of 69% and membrane thickness of 80 μm.

B. Surface treatment of the porous membrane for suppressing protein adsorption

Argon plasma (100 W, 0.1 Torr, 15 sec.) was irradiated to the polypropylene porous membrane thus obtained, which was then brought into contact with 2-methoxyethyl acrylate gas (1.0 Torr) for 3 minutes and then with glycidyl acrylate gas (0.7 Torr) for 1 minute to perform surface graft polymerization. As a result, hydrophilic porous membrane having reactive functional groups on the surface was obtained.

C. Immobilization of polyamine compound

As the next step, this porous membrane was immersed for 18 hours at 60° C. in an aqueous solution containing 1 wt. % spermidine and 0.5 wt. % pyridine as catalyst to immobilize spermidine on the membrane surface. The membrane obtained was washed thoroughly with methanol and used as the test sample. Spermidine bound to poly-(2-methoxyethyl acrylate) and glycidyl groups introduced into the surface of the polypropylene membrane was confirmed by IR (ATR method), NMR and ESCA. The membrane had the void volume of 65%, water transmission rate of 380 ml/min/m²/mmHg and the maximum pore diameter of 0.5 μm.

D. Measurement of virus removal rate

This membrane was set in a Swin-Lock filter holder (manufactured by Nuclepore) (φ25 mm), and using the membrane, 10 ml of PBS buffer (pH 7.35–7.6) containing about $10^4$ PFU/ml of herpes virus type I H.F. strain and 10 ml of plasma sampled from human fresh blood were filtrated to determine the virus removal rate of the membrane. The virus removal rate was 99.9% or more in PBS buffer and 99% in human plasma. When similar test was performed on φX174 (bacteriophage), the removal rates of 99.9% or more in PBS buffer and 99% in human plasma were demonstrated.

EXAMPLE 2

Except for 1 wt. % spermine used instead of spermidine, the same procedure as shown in steps A through C in Example 1 was performed to obtain a porous membrane. This membrane had the void volume of 64%, water transmission rate of 380 ml/min/m²/mmHg and the maximum pore diameter of 0.5 μm.

This membrane was set in a Swin-Lock filter holder (φ25 mm), and using the membrane, 10 ml of PBS buffer (pH 7.35–7.6) containing about $10^4$ PFU/ml of hepes virus type I H.F strain and 10 ml of plasma sampled from human fresh blood were filtrated to determine the virus removal rate of the membrane. The virus removal rate was 99.9% or more in PBS buffer and 99% in human plasma. When similar test was performed on φX174, the removal rates of 99.9% or more in PBS buffer and 98% in human plasma were demonstrated.

EXAMPLE 3

A solution prepared by dissolving 18 parts by weight of polyvinylidene fluoride powder (manufactured by Mitsubishi Yuka, Kynar K 301) in 73.8 parts by weight of acetone and 8.2 parts by weight of dimethylformamide was cast over a polyethylene terephtalate film. This was immersed in a 1,1,2-trichlorotrifluoroethane solution for 5 minutes and then dried to obtain a polyvinylidene fluoride porous membrane having the membrane thickness of 125 μm and the maximum pore diameter of 0.45 μm.

This polyvinylidene fluoride porous membrane was treated in the same manner as described in the step B of Example 1 for graft polymerization of 2-methoxyethyl acrylate to the membrane surface, and processed as shown in the step C of Example 1 to obtain a membrane in which spermidine was immobilized. This membrane had the void volume of 71%, water transmission rate of 430 ml/min/m²/mmHg and the maximum pore diameter of 0.45 μm.

This membrane was set in a swin-Lock filter holder (φ25 mm), and using the membrane, 10 ml of PBS buffer (pH 7.35–7.6) containing about $10^4$ PFU/ml of herpes virus type I H.F. strain and 10 ml of plasma sampled from human fresh blood were filtrated to determine the virus removal rate of the membrane. The virus removal rate was 99.9% or more in PBS buffer and 98% in human plasma. When similar test was performed on φX174, the removal rates of 99.9% or more in PBS buffer and 98% in human plasma were demonstrated.

EXAMPLE 4

Polypropylene unwoven cloth (manufactured by Tonen Co., Ltd., Tapirus) was treated by the steps B and C in Example 1 to obtain a membrane in which spermidine was immobilized.

Twenty pieces of this membrane were laminated and set in a Swin-Lock filter holder (φ25 mm), and using the membrane, 10 ml of PBS buffer (pH 7.35–7.6) containing about $10^4$ PFU/ml of herpes virus type I H.F. strain and 10 ml of plasma sampled from human fresh blood were filtrated to determine the virus removal rate of the membrane. The virus removal rate was 99.9% or more in PBS buffer and 99% in human plasma. When similar test was performed on φX174, the removal rates of 99.9% or more in PBS buffer and 99% in human plasma were demonstrated.

EXAMPLE 5

After irradiation of argon plasma (100 W, 0.1 Torr, 15 sec.), the polypropylene porous membrane obtained by the step A of Example 1 was brought into contact with glycidyl acrylate gas (0.7 Torr) for 5 minutes to perform surface graft polymerization. As a result, a hydrophilic porous membrane having reactive functional groups on the surface was obtained. Subsequently, this porous membrane was immersed for 5 hours at 60° C. in an aqueous solution containing 1 wt. % spermidine and 0.5 wt. % pyridine to immobilize spermidine on the membrane surface.

Three pieces of this membrane were laminated and set in a Swin-Lock filter holder (φ25 mm), and using the membrane, 10 ml of PBS buffer (pH 7.35–7.6) containing about $10^4$ PFU/ml of herpes virus type I H.F. strain and 10 ml of plasma sampled from human fresh blood were filtrated to determine the virus removal rate of the membrane. The virus removal rate was 99.9% or more in PBS buffer and 91% in human plasma. When similar test was performed on φX174, the removal rates of 99.9% or more in PBS buffer and 90% in human plasma were demonstrated.

Comparative Example 1

Surface graft polymerization of 2-methoxyethyl acrylate and glycidyl acrylate was performed on the membrane by the method described in the steps A and B of Example 1, and the virus removal rate was determined by the method described in the step D of Example 1 without immobilizing polyamine compound.

The removal rates of herpes virus and φx174 in PBS buffer and human plasma were both 50% or lower.

Comparative Example 2

After irradiation of argon plasma (100 W, 0.1 Torr, 15 sec.), the polypropylene porous membrane obtained from the step A in Example 1 was brought into contact with 2-methoxyethyl acrylate gas (0.8 Torr) for 3 minutes and 4-vinylpyridine gas (0.8 Torr) for 2 minutes for surface graft polymerization. By treating the membrane for production of quaternary ammonium in methanol containing 0.1 mol of benzylchloride at 55° C. for 3 hours, a porous membrane having pyridinium structure on the surface was obtained. This membrane had the void volume of 63%, water transmission rate of 120 ml/min/m²/mmHg and the maximum pore diameter of 0.5 μm.

When the virus removal rate of this porous membrane was determined by the method used in Example 1, the removal rate of 99% or more was demonstrated in PBS buffer against herpes virus and φX174, but the removal rate of against both was 50% or lower in human plasma.

EXAMPLE 6

A. Manufacture of polypropylene porous membrane

The same procedure as described in the step A of Example 1 was performed to obtain a polypropylene porous membrane having the maximum pore diameter of 0.5 μm, void volume of 58% and membrane thickness of 80 μm.

B. Surface processing of porous membrane for suppressing protein adsorption

After irradiating argon plasma (100 W, 0.1 Torr, 15 sec.), surface graft polymerization was performed on the polypropylene filter thus obtained by bringing it into contact with 2-methoxyethyl acrylate gas (1.0 Torr) for 3 minutes and subsequently with glycidyl acrylate gas (0.7 Torr) for 3 minutes. As a result, hydrophilic porous membrane having reactive functional groups on the surface was obtained.

C. Immobilization of polyamine compound

By immersing this porous membrane for 18 hours at 60° C. in an aqueous solution containing 1 wt. % polyethyleneimine (molecular weight 1,800) and 1.0 wt. % pyridine, polyethyleneimine was immobilized on the membrane surface. The membrane obtained was thoroughly washed with water and methylene chloride/methanol azeotropic solvent.

Polyethyleneimine bound to glycidyl groups and poly(2-methoxyethyl acrylate) introduced to the surface of porous membrane were confirmed by IR (ATR method). The N/C ratio obtained by ESCA was 0.06. The amount of amine obtained by perchloric acid titration was $3.3 \times 10^{-4}$ eq/g. This membrane had the void volume of 55%, water transmission rate of 390 ml/min/m²/mmHg and the maximum pore diameter of 0.52 μm.

D. Measurement of virus removal rate

This membrane was set in a Swin-Lock filter holder (φ25 mm), and using the membrane, 10 ml of PBS buffer (pH 7.35–7.6) containing about $10^4$ PFU/ml of herpes virus type I H.F. strain and 10 ml of plasma sampled from human fresh blood were filtrated to determine the virus removal rate of the membrane. The virus removal rate was 99.9% or more in PBS buffer and 99.9% in human plasma. When similar test was performed on φX174, the removal rates of 99.9% or more in PBS buffer and 99.8% in human plasma were demonstrated.

EXAMPLE 7

Using polyvinylidene fluoride filter (manufactured by Millipore) as the porous membrane, and except for using glycidyl methacrylate instead of glycidyl acrylate and polyethyleneimine having the molecular weight of 70,000 instead of polyethyleneimine with the molecular weight of 1,800, the same procedure as described in steps B and C in Example 6 was performed. As a result, a polyvinylidene fluoride filter in which polyethyleneimine (molecular weight 70,000) was immobilized on the surface of filter was prepared. The N/C ratio of this membrane determined by ESCA was 0.08 and the amount of amine obtained by perchloric acid titration was $4.8 \times 10^{-4}$ eq/g. This membrane had the void volume of 61%, water transmission rate of 380 ml/min/m²/mmHg and the maximum pore diameter of 0.50 μm.

This membrane was set in a Swin-Lock filter holder (φ25 mm), and using the membrane, 10 ml of PBS buffer (pH 7.35–7.6) containing about $10^4$ PFU/ml of herpes virus type I H.F. strain and 10 ml of plasma sampled from human fresh blood were filtrated to determine the virus removal rate of the membrane. The virus removal rate was 99.9% or more in PBS buffer and 99.9% in human plasma. When similar test was performed on φX174, the removal rates of 99.9% or more in PBS buffer and 99.8% in human plasma were demonstrated.

EXAMPLE 8

After irradiating argon plasma (100 W, 0.2 Torr, 20 sec.), surface graft polymerization was performed on the polypropylene porous membrane obtained from the step A in Example 6 by bringing it into contact with glycidyl acrylate gas (0.7 Torr) for 3 minutes. As a result a hydrophilic porous membrane having reactive functional groups on the surface was obtained.

This porous membrane was immersed in an aqueous solution containing 1 wt. % polyethyleneimine (molecular weight 70,000) and 0.5 wt. % pyridine at 60° C. for 18 hours to immobilize polyethyleneimine on the membrane surface. The membrane obtained was thoroughly washed with water and methylene chrolide/methanol azeotropic solvent and used as the test sample. This membrane had the void volume of 57%, water transmission rate of 352 ml/min/m²/mmHg and the maximum pore diameter of 0.49 μm. The N/C ratio obtained by ESCA was 0.07 and the amount of amine obtained by perchloric acid titration was $4.4 \times 10^{-4}$ eq/g.

This membrane was set in a Swin-Lock filter holder (φ25 mm), and using the membrane, 10 ml of PBS buffer (pH 7.35–7.6) containing about $10^4$ PFU/ml of herpes virus type I H.F. strain and 10 ml of plasma sampled from human fresh blood were filtrated to determine the virus removal rate of the membrane. The virus removal rate was 99.9% or more in PBS buffer and 98.3% in human plasma. when similar test was performed on φx174 and HIV, the removal rates of 99.9% or more in PBS buffer and 99.8% in human plasma against both were demonstrated.

EXAMPLE 9

Except that polyallylamine (molecular weight 10,000) as a polyamine compound was used instead of polyethyleneimine, the same procedure as described in the steps A through C of Example 6 was performed to obtain a polypropylene porous membrane in which polyarylamine was immobilized on the surface. This membrane had the void volume of 56%, water transmission rate of 348 ml/min/m²/mmHg and the maximum pore diameter of 0.49 μm. The N/C ratio of this membrane obtained by ESCA was 0.05 and the amount of amine obtained by perchloric acid titration was $5.1 \times 10^{-4}$ eq/g.

This membrane was set in a Swin-Lock filter holder (φ25 mm), and using the membrane, 10 ml of PBS buffer (pH 7.35–7.6) containing about $10^4$ PFU/ml of herpes virus type I H.F. strain and 10 ml of the plasma sampled from human fresh blood were filtrated to determine the virus removal rate of the membrane. The virus removal rate was 99.9% or more in PBS buffer and 99.6% in human plasma. When similar test was performed on φX174 and HIV, the removal rates of 99.9% or more in PBS buffer and 99.8% in human plasma against both were demonstrated.

EXAMPLE 10

Except that the polypropylene unwoven cloth (manufactured by Tonen Co., Ltd., Tapirns) was used as a membrane and polyethyleneimine (molecular weight 1,200) as a polyamine compound was used, the same procedure as described in the steps B and C of Example 6 was performed and the membrane in which polyethyleneimine (molecular weight 1,200) was immobolized was obtained.

Thirty pieces of this membrane were laminated and set in a Swin-Lock filter holder (φ25 mm), and using the membrane, 10 ml of PBS buffer (pH 7.35–7.6) containing about $10^4$ PFU/ml of herpes virus type I H.F. strain and 10 ml of the plasma sampled from human fresh blood were filtrated to determine the virus removal rate of the membrane. The virus removal rate was 99.9% or more in PBS buffer and 98.3% in human plasma. When similar test was performed on φX174, the removal rates of 99.9% or more in PBS buffer and 99.7% in human plasma were demonstrated.

EXAMPLE 11

Except for using polyethyleneimine having molecular weight of 70,000 as a polyamine compound, the same procedure as described in the steps B and C of Example 6 was performed on a polyurethane porous filter (manufactured by Toyo Polymer Co., Ltd., Rubicell) and the membrane in which polyethyleneimine (molecular weight 70,000) was immobilized was obtained. This membrane had the void volume of 82%, water transmission rate of $1.1 \times 10^4$ ml/min/m²/mmHg and the maximum pore diameter of 18 μm. The amount of amine obtained by perchloric acid titration was $1.6 \times 10^{-4}$ eq/g.

Twenty pieces of this membrane were laminated and set in a Swin-Lock filter holder (φ25 mm), and using the membrane, 30 ml of PBS buffer (pH 7.35–7.6) containing about $10^4$ PFU/ml of herpes virus type I H.F. strain and 30 ml of plasma sampled from human fresh blood were filtrated to determine the virus removal rate of the membrane. The virus removal rate was 99.9% or more in PBS buffer and 99.1% in human plasma. When similar test was performed on φX174, the removal rates of 99.9% or more in PBS buffer and 99.4% in human plasma were demonstrated.

Comparative Example 3

The same procedure as described in the steps A and B in Example 6 was performed to obtain a polypropylene porous membrane having 2-methoxyethyl acrylate and glycidyl acrylate graft-polymerized on the surface of the membrane. This membrane had the void volume of 59%, water transmission rate of 434 ml/min/m²/mmHg and the maximum pore diameter of 0.5 μm.

The virus removal rate of this membrane was measured by performing the same procedure as described in the step D in Example 6 but without immobilizing a polyamine compound on the membrane surface. The removal rates of herpes virus and φX174 in PBS buffer and plasma were both 50% or lower.

Comparative Example 4

Except that polyethyleneimine having an average molecular weight of 1,200 was used as a polyamine compound, and immobilization was performed at 60° C. for 1 hour on the porous membrane obtained by the same procedure as described in steps A and B in Example 6, the same procedure as in the step C in Example 6 was performed, and the membrane in which polyethyleneimine was immobilized on the surface was prepared. This membrane had the void volume of 57%, water transmission rate of 365 ml/min/m²/mmHg and the maximum pore diameter of 0.50 μm. The N/C ratio obtained by ESCA was 0.004 and the amount of amine obtained by perchloric acid titration was $0.7 \times 10^{-4}$ eq/g.

By performing the same procedure as described in the step D in Example 6, the virus removal rate of this membrane was measured. The removal rates of herpes virus in PBS buffer and human plasma were respectively 99.9% and 50% or less. The respective removal rates of φX174 were 99.9% and 50% or less.

As shown in the above, this membrane is highly capable of removing the virus in the water but does not demonstrate satisfactory function of removing virus from plasma.

Comparative Example 5

After irradiating argon plasma (100 W, 0.1 Torr, 15 sec.), the polypropylene porous membrane obtained from step A in Example 6 was brought into contact with 2-methoxyethyl acrylate (0.8 Torr) for 3 minutes and then with 4-vinylpyridine (0.8 Torr) for 2 minutes for surface graft polymerization.

Then this membrane was treated in methanol containing 0.1 mol of benzyl chloride at 55° C. for 3 hours, and as a result, a membrane having pyridinium structure on the surface was obtained. This membrane had the void volume of 57%, water transmission rate of $1 \times 10^4$ ml/min/m²/mmHg and the maximum pore diameter of 0.48 μm.

When the virus removal rate of this membrane was measured by the same method as described in step D of Example 6, the removal rate of 99.9% against herpes virus and φX174 was demonstrated in PBS buffer, but the rate went down to 50% or lower in human plasma.

EXAMPLE 12

A. Preparation of porous membrane
i) Porous membrane test sample 1

Soxhlet washing of polyurethane porous body having the maximum pore diameter of 18 μm and the void volume of 86% (manufactured by Toyo Polymer, Rubicell) was performed with methanol to remove impurities present in the membrane. The porous body was thoroughly dried, and then irradiated with low temperature plasma (ArO, 2 Torr) for 20 seconds, after which surface graft polymerization was done by supplying glycidyl methacrylate gas for reaction at the temperature of 288K for 5 minutes. This porous body was then immersed in an aqueous solution (containing 1 wt. % pyridine) of 1 wt. % polyethyleneimine (molecular weight 1,200) at 60° C. for 18 hours. This was then washed well with ion-exchanged water and dried to be used as the test sample 1.

ii) Porous membrane test sample 2

Except that polyethyleneimine with molecular weight of 1,800 was used as a polyamine compound, the same method used for the above test sample 1 was carried out to obtain the test sample 2.

iii) Preparation of porous membrane test sample 3

Except that 1% pyridine solution which did not contain polyethyleneimine was used instead of 1 weight % aqueous solution of polyethyleneimine, the same method used for the above test sample 1 was carried out to obtain the test sample 3.

iv) Porous membrane test samples 4–8

Test samples 4–8 were prepared by immobilizing, respectively, Cationon UK (manufactured by Ipposha Yushi Industry), Panfix PX, or poly(1-ethylimino-2 -guanydinoimidazole monohydrochloride) (manufactured by the same), polyehtyleneimine (average molecular weight 300), polyethyleneimine (average molecular weight 10,000) or polyethyleneimine (average molecular weight 7,000) on a polyurethane porous body having the maximum pore diameter of 18 μmm and void volume of 86% (manufactured by Toyo Polymer, Rubicell) according to the same method used for the test sample 1. Cationon UK immobilized on the test sample 4 and Panfix PX immobilized on the test sample 5 were as follows.

Cationon UK

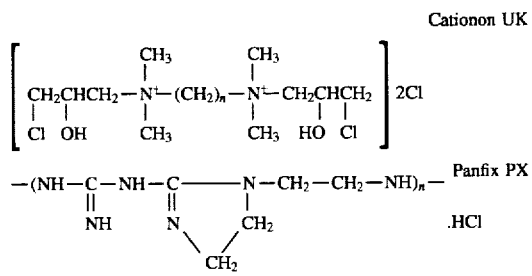

v) Porous membrane test sample 9

Surface graft polymerization was performed by irradiating polyurethane porous body having the maximum pore diameter of 18 μmm and void volume of 86% (manufactured by Toyo Polymer, Rubicell) with low temperature plasma (ArO, 2 Torr) for 20 seconds, and then supplying it with vinyl pyridine gas for reaction at the temperature of 288K for 5 minutes. The porous body was then treated with 1% benzyl chloride in methanol solution at 55° C. for 3 hours to produce quaternary amine. As a result, the test sample 9 having poly N-benzylvinylpyridinium chloride on the surface was obtained.

B. Measurement of leukocyte and platelet removal rates

A disk measuring 0.6 mm in thickness and 25 mm in diameter was punched out from each of the porous bodies obtained by the step A in the above. Each disk was used as a filter material 5 of the blood filter having the configuration shown in FIG. 1. The effective area of each blood filter was 3.4 cm². Using these blood filters, a device whose configuration is roughly shown in FIG. 2 was assembled.

Using this device, a concentrated erythrocyte solution prepared from fresh blood added with CPD (citrate phosphate dextrose) of a normal person (leukocyte: $3.0 \times 10^3$–$5.0 \times 10^3$, platelet: $1.0 \times 10^5$–$3.0 \times 10^5$, erythrocyte: $3.0 \times 10^6$–$5.0 \times 10^6$) was passed through the blood filter 1 at the flow rate of 1.2 ml/min, and the leukocyte count and platelet count before and after passing through the filter were determined by an automatic blood corpuscle counter (manufactured by Toa Medical Electric Co., Ltd., Sysmex NE-600). Based on the values obtained, the removal rates of leukocytes and platelets were obtained by the following formulae (C) and (D) for each filter.

Leukocyte removal rate (%)={1−(leukocyte count after filtration/leukocyte count before filtration)}×100    (C)

Platelet removal rate (%)={1−(platelet count after filtration/platelet count before filtration)}×100    (D)

Furthermore, β-TG and serotonin which are factors released from platelets upon activation were also measured using β-TG RIA kit (available from Radiochemical Center, Amersham, England). To be more precise, freeze-dried $^{126}$I-β-TG (human) was dissolved in distilled water. separately, freeze-dried anti-human β-TG anti-serum was also dissolved in distilled water. Furthermore, freeze-dried β-TG standard substance in respective amounts prescribed for measurement was also dissolved in distilled water to prepare a standard concentration solutions. Aqueous $^{126}$I-β-TG (human) solution was placed in a test tube containing a buffer comprising EDTA and theophylline, to which anti-human β-TG antiserum was added for agitation for several seconds. This was left standing at room temperature for 1 hour, and then added with ammonium sulfate solution for further several seconds of agitation. After 10–60 minutes, this was centrifuged and precipitated at room temperature and 1500 G for 20 minutes, and the supernatant was discarded. The sediments obtained were determined of their count by δ-scintillation counter. The value was divided by the total count to obtain the bonding ratio (%). Separately, a standard curve was prepared from the bonding ratio of the standard substance, and the concentration of β-TG of each sample was calculated by this standard curve. The concentration of serotonin was determined by HPLC method (clin. chem., vol. 30, 1984, page 131).

The results are shown in the Table 1 below.

TABLE 1

| Test sample | Immobilized compound | Leutocyte removal rate (%) | Platelet removal rate (%) | β-TG concentration in the filtrate (ng/ml) | Serotonin concentration in the filtrate (ng/ml) |
|---|---|---|---|---|---|
| 1 | Polyethyleneimine Mw = 1200 | 99.79 | 99.09 | 340 | 7 or less |
| 2 | Polyethyleneimine Mw = 1800 | 99.36 | 98.69 | 350 | 7 or less |
| 3 | Unprocessed | 86.77 | 21.74 | 320 | 7 or less |
| 4 | Cationon UK | 99.84 | 99.17 | 3900 | 34 |
| 5 | Panfix PX | 99.90 | 90.14 | 5000 | 40 |
| 6 | Polyethyleneimine Mw = 300 | 96.65 | 78.28 | 340 | 7 or less |

TABLE 1-continued

| Test sample | Immobilized compound | Leukocyte removal rate (%) | Platelet removal rate (%) | β-TG concentration in the filtrate (ng/ml) | Serotonin concentration in the filtrate (ng/ml) |
|---|---|---|---|---|---|
| 7 | Polyethyleneimine Mw = 10000 | 99.04 | 98.89 | 670 | 7 or less |
| 8 | Polyethyleneimine Mw = 70000 | 98.92 | 94.24 | 1100 | 7 or less |
| 9 | Poly-N-benzylvinyl-pyridinium chloride | 97.36 | 93.28 | 2400 | 30 |

As is clear from Table 1, the blood filters respectively using the test sample 1 and 2 have higher platelet removal rate and leukocyte removal rate compared with those by the blood filter using the test sample 3. Furthermore, no remarkable increase in β-TG value and serotonin value which are the indices of platelet activation was observed.

Despite the similar leukocyte and platelet removal rates, a remarkable increase in β-TG value and serotonin value was observed in the blood filters respectively using the test samples 4 and 5 compared with that using the above test sample 1 or 2.

Though β-TG value and serotonin value were not increased, the platelet removal rate of the blood filter using the test sample 6 was not as improved as that of the blood filter using the test sample 1 or 2.

Compared with the blood filter using the test sample 1 or 2, the blood filters respectively using the test samples 7 and 8 indicated an increase in β-TG value even though the leukocyte removal rate and platelet removal rate were similar.

Compared with blood filter using the test sample 1 or 2, the blood filter using the test sample 9 demonstrated a remarkable increase in β-TG value and serotonin value which indicate activation of platelets despite the similar platelet and leukocyte removal rates.

What is claimed is:

1. A material which removes viruses from a protein containing solution comprising a base material, a surface graft radical introduced onto a surface of said base material and a polyamine compound immobilized on a surface of the base material through the surface graft radical, wherein said polyamine compound is at least one type of compound selected from the group consisting of:

(a) a polyamine compound which has primary and secondary amines in its molecule and a hydrophobic part between these amines, (b) a polyamine compound represented by the following formula (I):

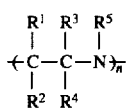

wherein $R^1$, $R^2$, $R^3$, $R^4$ and $R^5$ independently represent substituents selected from the group consisting of hydrogen, aliphatic and aromatic hydrocarbons, and halogen, and n is 5 or more, and (c) a polyamine compound represented by the following formula (II):

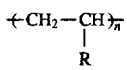

wherein R represents $NH_2$ or an aminoalkyl group having 1 to 4 carbon atoms and n is 5 or more.

2. The material according to claim 1, which is in the form of porous membrane.

3. A blood filter comprising a housing which has an inlet and outlet, and the material according to claim 1, which is arranged inside said housing and is in the form of porous membrane.

4. The blood filter according to claim 3, wherein the maximum pore diameter of said porous membrane ranges from 5–50 μm.

5. A material which removes viruses from a protein containing solutions comprising a base material, a surface graft radical introduced onto a surface of said base material and a polyamine compound immobilized on a surface of the base material through the surface graft radical, wherein said polyamine compound is at least one type of compound selected from the group consisting of:

(a) a polyamine compound which has primary and secondary amines in its molecule and a hydrophobic part between these amines, (b) a polyamine compound represented by the following formula (I);

wherein $R^1$, $R^2$, $R^3$, $R^4$ and $R^5$ independently represent substituents selected from the group consisting of hydrogen, aliphatic and aromatic hydrocarbons, and halogen, and n is 5 or more, and (c) a polyamine compound represented by the following formula (II):

wherein R represents $NH_2$ or an aminoalkyl group having 1 to 4 carbon atoms and n is 5 or more, and wherein said surface graft radical is a graft chain composed of a monomer having at least one radical selected from the group consisting of an acid halogen, an isocyanate and an epoxy radical in its molecule as a reactive functional group.

6. The material according to claim 5, wherein said monomer is provided in gaseous form.

7. The material according to claim 6, wherein said gaseous monomer is added at a pressure ranging from 0.001 to 100 Torr.

* * * * *

UNITED STATES PATENT AND TRADEMARK OFFICE
CERTIFICATE OF CORRECTION

PATENT NO. : 5,547,576
DATED : August 20, 1996
INVENTOR(S) : Makoto ONISHI et al It is certified that error appears in the above-indentified patent and that said Letters Patent is hereby corrected as shown below:

In Column 4, line 60, delete "Bachtach" and insert -- Bachrach --.
In Column 4, line 61, delete "Helmet" and insert -- Heimer --.

Signed and Sealed this

Twenty-fifth Day of February, 199

Attest:

BRUCE LEHMAN

*Attesting Officer*    *Commissioner of Patents and Trademarks*